(12) United States Patent
Ren et al.

(10) Patent No.: US 12,224,045 B2
(45) Date of Patent: Feb. 11, 2025

(54) SYSTEMS AND METHODS FOR PREDICTION OF PROTEIN FORMULATION PROPERTIES

(71) Applicant: AMGEN INC., Thousand Oaks, CA (US)

(72) Inventors: Cindy Ren, Calabasas, CA (US); Mohan B. Boggara, Thousand Oaks, CA (US); Nitin Rathore, Thousand Oaks, CA (US); Behnam Partopour, Cambridge, MA (US)

(73) Assignee: AMGEN INC., Thousand Oaks, CA (US)

( * ) Notice: Subject to any disclaimer, the term of this patent is extended or adjusted under 35 U.S.C. 154(b) by 423 days.

(21) Appl. No.: 17/638,395

(22) PCT Filed: Aug. 25, 2020

(86) PCT No.: PCT/US2020/047755
§ 371 (c)(1),
(2) Date: Feb. 25, 2022

(87) PCT Pub. No.: WO2021/041384
PCT Pub. Date: Mar. 4, 2021

(65) Prior Publication Data
US 2022/0293223 A1 Sep. 15, 2022

Related U.S. Application Data

(60) Provisional application No. 62/891,541, filed on Aug. 26, 2019.

(51) Int. Cl.
*G16C 20/30* (2019.01)
*G16C 20/50* (2019.01)
*G16C 20/70* (2019.01)

(52) U.S. Cl.
CPC ............ *G16C 20/30* (2019.02); *G16C 20/50* (2019.02); *G16C 20/70* (2019.02)

(58) Field of Classification Search
CPC ........ G16C 20/70; G16C 20/50; G16C 20/30; G16B 15/20
See application file for complete search history.

(56) References Cited

U.S. PATENT DOCUMENTS

| 9,285,363 B2 * | 3/2016 | Salemme | B82Y 30/00 |
| 10,497,466 B2 * | 12/2019 | Shilov | G16B 20/00 |
| 2010/0280759 A1 * | 11/2010 | Kagan | G16B 45/00 |
| | | | 702/19 |

OTHER PUBLICATIONS

Shan et al., "Developability Assessment of Engineered Monoclonal Antibody Variants With a Complex Self-Association Behavior Using Complementary Analytical and in Silico Tools", Molecular Pharmaceutics, vol. 15, No. 12, Dec. 3, 2018, pp. 5697-5710.

(Continued)

*Primary Examiner* — An H Do
(74) *Attorney, Agent, or Firm* — MARSHALL, GERSTEIN & BORUN LLP

(57) ABSTRACT

In a method for predicting a property of potential protein formulations, a set of formulation descriptors is classified as belonging to a specific one of a plurality of predetermined groups that each correspond to a different value range for a protein formulation property. Classifying the set of descriptors includes applying at least a first portion of the set of descriptors as inputs to a first machine learning model. The method also includes selecting, based on the classification, a second machine learning model from among multiple models corresponding to different groups. The method also includes predicting a value of the protein formulation property that corresponds to the set of descriptors, by applying at least a second portion of the set of formulation descriptors as inputs to the selected model. The method further includes (Continued)

causing the value of the protein formulation property to be displayed to a user and/or stored in a memory.

21 Claims, 8 Drawing Sheets

(56) References Cited

OTHER PUBLICATIONS

Agrawal et al., "Computational Tool for the Early Screening of Monoclonal Antibodies for Their Viscosities", mAbs, vol. 8, No. 1, Sep. 23, 2015, pp. 43-48.
Barata et al., "Identification of Protein-Excipient Interaction Hotspots Using Computational Approaches", International Journal of Molecular Sciences, vol. 17, No. 6, Jun. 1, 2016, p. 853.
Chi et al., "Physical Stability of Proteins in Aqueous Solution: Mechanism and Driving Forces in Nonnative Protein Aggregation", Pharmaceutical Research, vol. 20, No. 9, Sep. 2003, pp. 1325-1336.
Wei Wang, "Instability, Stabilization, and Formulation of Liquid Protein Pharmaceuticals", International Journal of Pharmaceutics, vol. 185, 1999, pp. 129-188.
Christopher J. Roberts, "Therapeutic Protein Aggregation: Mechanisms, Design, and Control", Trends in Biotechnology, vol. 32, No. 7, Jul. 2014, pp. 372-380.
Search Report and Written Opinion in International Application No. PCT/US2020/047755 dated Oct. 23, 2020, 26 pages.

\* cited by examiner

SYSTEMS AND METHODS FOR PREDICTION OF PROTEIN FORMULATION PROPERTIES

FIELD OF DISCLOSURE

The present application relates generally to formulation development for protein-based biologics, and more specifically to techniques for optimizing protein formulations.

BACKGROUND

Protein-based pharmaceuticals are among the fastest growing therapeutic agents in (pre)clinical development and as commercial products. In comparison with small chemical drugs, protein pharmaceuticals have high specificity and typically provide therapy to high impact diseases, such as various cancers, auto-immune diseases, and metabolic disorders (Roberts, Trends Biotechnol. 2014 10 Jul.; 32(7):372-80, Wang, Int J Pharm. 1999 Aug. 20; 185(2):129-88).

Protein-based pharmaceuticals, such as recombinant proteins, can now be obtained in high purity when first manufactured due to advances in commercial scale purification processes. However, proteins are labile molecules and are susceptible to degradation, both chemical and physical. Chemical degradation refers to modifications involving covalent bonds, such as deamidation, oxidation, cleavage or formation of new disulfide bridges, hydrolysis, isomerization, or deglycosylation. Physical degradation includes protein unfolding, undesirable adsorption to surfaces, and aggregation. Optimizing for physical and chemical stability is one of the most challenging tasks in the development of protein pharmaceuticals (Chi et al., Pharm Res, Vol. 20, No. 9, September 2003, pp. 1325-1336, 20 Roberts, Trends Biotechnol. 2014 July; 32(7):372-80). In order to do so, the protein concentration, specific excipients and solution properties of the final drug substance and drug product must be identified to ensure that a reasonable shelf life can be achieved as well as to ensure manufacturability and device compatibility.

FIG. 1 depicts the typical development process 10 for a drug product formulation. After a specific molecule is chosen for a given indication at stage 12, a number of different candidate formulations (e.g., different solution pH levels, different excipient types, etc.) are considered for use with the molecule, and screened to find the top/best candidate formulations. More specifically, the candidate formulations are screened to optimize for viscosity, as well as product quality attributes relating to activity and chemical and physical stability (e.g., in terms of chemical structure/properties) of the molecule/formulation combination over time and at various temperatures. While increasing the protein concentration within formulations offers many advantages, such as subcutaneous administration (enabling at-home administration) and reduced dosing frequency, significant technical challenges must be overcome, including minimization of viscosity (critical in device compatibility and manufacturability) and preservation of stability, both of which are key aspects in ensuring a commercially viable product.

Due to the complex intraprotein, protein-excipient and protein-solvent interactions, empirical testing is typically required at stage 14 to measure viscosity, stability and activity for each formulation. This testing requires a very substantial investment of time, resources and materials, and can become a significant bottleneck in drug product development. At the same time, it is critical to develop and optimize formulations as soon as possible, in order to deliver a drug product to the clinic and to the market (or otherwise in use) in a timely manner.

At stage 16, the top candidates from the empirical testing at stage 14 are produced at larger-scale, e.g., to characterize and verify performance at representative scales, over longer durations, and over a wider range of temperatures. Based on the results from the screening and larger-scale studies at stage 16, the commercial formulation recommendation is selected for commercial production.

SUMMARY

Embodiments described herein relate to systems and methods that, among other potential uses (e.g., pure research applications) facilitate protein formulation optimization for drug product development. In particular, useful formulation descriptors (which can include product molecule/protein descriptors, excipient descriptors, and/or solution descriptors) are identified, and historical data corresponding to those descriptors is used to train machine learning models to predict values of one or more specific protein formulation properties, such as viscosity and product quality attributes. To increase the accuracy of a given prediction, a two-stage approach is used. For the first stage, a machine learning model classifies a set of formulation descriptors as one of a predetermined number of "groups," with each group corresponding to a different range of likely or expected values of a given property (e.g., viscosity, or a chromatography-based stability metric, etc.). For the second stage, a second machine learning model predicts a value of the property (e.g., a viscosity value in units of centipoise, or cP). The second machine learning model is selected from among two or more trained models, with each such model corresponding to a different one of the predetermined groups. That is, each group-specific model is specifically trained to accurately predict formulation property values within a particular, constrained range of values for the given property. For example, the second stage may selectively apply a machine learning model trained to predict viscosity values in the 0.5-15 cP range, a machine learning model trained to predict viscosity values in the 15-30 cP range, or a machine learning model trained to predict viscosity values in the 30-110 cP range, depending on which group/range resulted from the classification at the first stage. Some or all of the machine learning models at the second stage (and possibly also the first stage) may be regression models, such as random forest models.

This technique allows for much faster screening of candidate protein formulations as compared to the conventional process 10, without necessarily requiring empirical testing, and without overly compromising accuracy. Thus, the development cycle (e.g., as discussed above with reference to FIG. 1) may be greatly shortened, and the expenditure of time, materials, and labor may be greatly reduced. Further, the two-stage approach described herein provides a solution to the problem of predicting viscosity and/or other protein formulation properties in a highly accurate manner, which has been a particular challenge. For example, the two-stage approach described herein can provide viscosity predictions with significantly higher accuracy than has been observed when using a single machine learning model.

BRIEF DESCRIPTION OF THE DRAWINGS

The skilled artisan will understand that the figures, described herein, are included for purposes of illustration and do not limit the present disclosure. The drawings are not necessarily to scale, and emphasis is instead placed upon illustrating the principles of the present disclosure. It is to be understood that, in some instances, various aspects of the described implementations may be shown exaggerated or enlarged to facilitate an understanding of the described implementations. In the drawings, like reference characters throughout the various drawings generally refer to functionally similar and/or structurally similar components.

DETAILED DESCRIPTION

The various concepts introduced above and discussed in greater detail below may be implemented in any of numerous ways, and the described concepts are not limited to any particular manner of implementation. Examples of implementations are provided for illustrative purposes.

Figure 2:
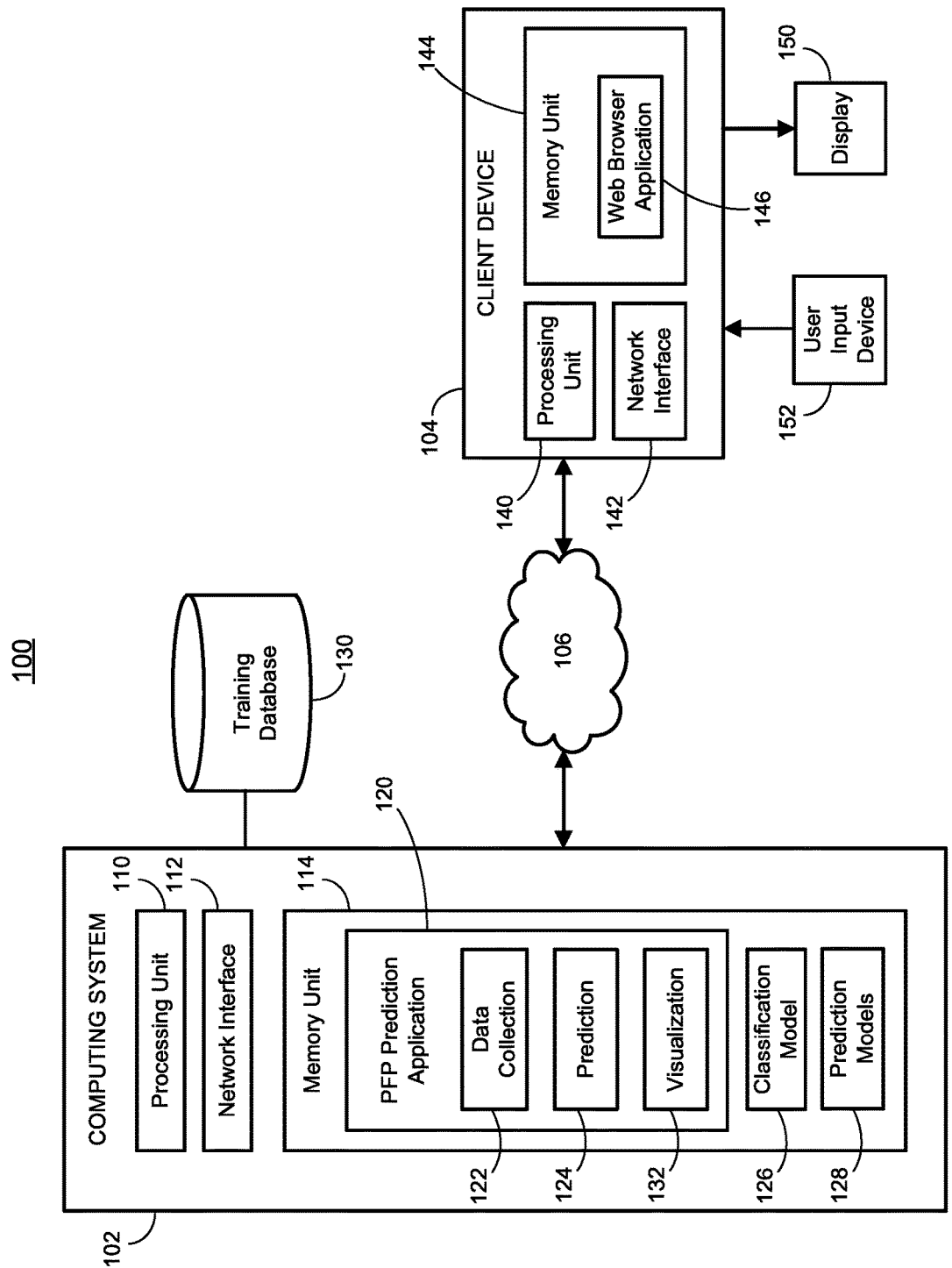
FIG. 2 is a simplified block diagram of an example system that may implement the techniques described herein.

FIG. 2 is a simplified block diagram of an example system 100 that may implement the techniques described herein. System 100 includes a computing system 102 communicatively coupled to a client device 104 via a network 106. Computing system 102 is generally configured to train machine learning models, and use those models to predict viscosity and/or other protein formulation properties based on different sets of formulation descriptors (including product molecule/protein descriptors, excipient descriptors, and/or solution descriptors). Client device 104 is generally configured to enable a user, who may be remote from computing system 102, to make use of the prediction capabilities of computing system 102, and to provide various interactive capabilities to the user as discussed further below. Network 106 may be a single communication network, or may include multiple communication networks of one or more types (e.g., one or more wired and/or wireless local area networks (LANs), and/or one or more wired and/or wireless wide area networks (WANs) such as the Internet). While FIG. 2 shows only one client device 104, other embodiments may include any number of different client devices communicatively coupled to computing system 102 via network 106. In particular, client device 104 and a number of other client devices may utilize the prediction capabilities of computing system 102 as a "cloud" service. Alternatively, computing server 102 may be a local server or set of servers, or client device 104 may include the components and functionality of computing system 102. In the latter case, system 100 may omit computing system 102 and network 106.

As seen in FIG. 2, computing system 102 includes a processing unit 110, a network interface 112, and a memory unit 114. In some embodiments, however, computing system 102 includes two or more computers that are either co-located or remote from each other. In these distributed embodiments, the operations described herein relating to processing unit 110, network interface 112, and/or memory unit 114 may be divided among multiple processing units, network interfaces and/or memory units, respectively.

Processing unit 110 includes one or more processors, each of which may be a programmable microprocessor that executes software instructions stored in memory unit 114 to execute some or all of the functions of computing system 102 as described herein. Processing unit 110 may include one or more central processing units (CPUs) and/or one or more graphics processing units (GPUs), for example. Alternatively, or in addition, some of the processors in processing unit 110 may be other types of processors (e.g., application-specific integrated circuits (ASICs), field-programmable gate arrays (FPGAs), etc.), and some of the functionality of computing system 102 as described herein may instead be implemented in hardware.

Network interface 112 may include any suitable hardware (e.g., front-end transmitter and receiver hardware), firmware, and/or software configured to communicate with client device 104 via network 106 using one or more communication protocols. For example, network interface 112 may be or include an Ethernet interface, enabling computing system 102 to communicate with client device 104 over the Internet or an intranet, etc.

Memory unit 114 may include one or more volatile and/or non-volatile memories. Any suitable memory type or types may be included, such as read-only memory (ROM), random access memory (RAM), flash memory, a solid-state drive (SSD), a hard disk drive (HDD), and so on. Collectively, memory unit 114 may store one or more software applications, the data received/used by those applications, and the data output/generated by those applications. These applications include a protein formulation property ("PFP") prediction application 120 that, when executed by processing unit 110, predicts one or more protein formulation properties for a given set of inputs (formulation descriptors). While various components of application 120 are discussed below, it is understood that those components may be distributed among different software applications, and/or that the functionality of any one such component may be divided among two or more software applications.

In general, a data collection unit 122 of PFP prediction application 120 collects formulation descriptors, which may be numerical and/or categorical parameters of various aspects of a (hypothetical/potential or real) formulation. For example, a set of formulation descriptors may include descriptors of a candidate product molecule, descriptors of a candidate excipient, and descriptors of a candidate solution. Data collection unit 122 may receive the descriptors from a user (e.g., a user of client device 104, as discussed below), or may read the descriptors from a file or database, for example.

For a given set of formulation descriptors, a prediction unit 124 of PFP prediction application 120 operates on the descriptors to predict a formulation property value. To do so, PFP prediction application 120 utilizes a classification model 126 and prediction models 128, which are also stored in memory unit 114 (or another suitable memory) and discussed in further detail below. In the depicted embodiments, computing system 102 trains classification model 126 and prediction models 128 using data (e.g., formulation descriptor sets with associated labels) stored in a training database 130, where training database 130 may represent a single database stored in a single memory device, multiple databases stored in multiple memory devices, or some combination thereof. In other embodiments, another computing system not shown in FIG. 2 (e.g., a remote server) trains classification model 126 and/or prediction models 128, and computing system 102 obtains the models 126, 128 via network 106 or by other means.

A visualization unit 132 of PFP prediction application 120 generates one or more graphical user interfaces (GUIs) that generally enable users to enter information (e.g., formulation descriptors), and/or to view information indicative of the predictions provided by prediction unit 124 (and/or other information derived from those predictions).

Client device 104 includes a processing unit 140, a network interface 142, and a memory unit 144. Processing unit 140 includes one or more processors, each of which may be a programmable microprocessor that executes software instructions stored in memory unit 144 to execute some or all of the functions of client device 104 as described herein. Processing unit 140 may include one or more CPUs and/or one or more GPUs, for example. Alternatively, or in addition, some of the processors in processing unit 140 may be other types of processors (e.g., ASICs, FPGAs, etc.), and some of the functionality of client device 104 as described herein may instead be implemented in hardware.

Network interface 142 may include any suitable hardware (e.g., a front-end transmitter and receiver hardware), firmware, and/or software configured to communicate with computing system 102 via network 106 using one or more communication protocols. For example, network interface 142 may be or include an Ethernet interface, enabling client device 104 to communicate with computing system 102 over the Internet or an intranet, etc.

Memory unit 144 may include one or more volatile and/or non-volatile memories. Any suitable memory type or types may be included, such as ROM, RAM, flash memory, an SSD, an HDD, and so on. Collectively, memory unit 144 may store one or more software applications, the data received/used by those applications, and the data output/generated by those applications. These applications include a web browser application 146 that, when executed by processing unit 140, enables the user of client device 104 to access various web sites and web services, including the services provided by computing system 102 when executing PFP prediction application 120.

A display 150 of client device 104 may implement any suitable display technology (e.g., LED, OLED, LCD, etc.) to present information to a user, and a user input device 152 of client device 104 may be a keyboard, mouse, and/or any other suitable input device(s). In some embodiments, display 150 and user input device 152 are integrated within a single device (e.g., a touchscreen display). Generally, display 150 and user input device 152 may collectively enable a user to interact with GUIs provided by client device 104 (and indirectly provided by computing system 102 via the web service), e.g., as discussed below with reference to FIGS. 6A and 6B. In some embodiments, however, system 100 does not implement web services. For example, as noted above, the operations described herein may all be performed at client device 104, and computing system 102 and network 106 may be omitted.

Figure 1:
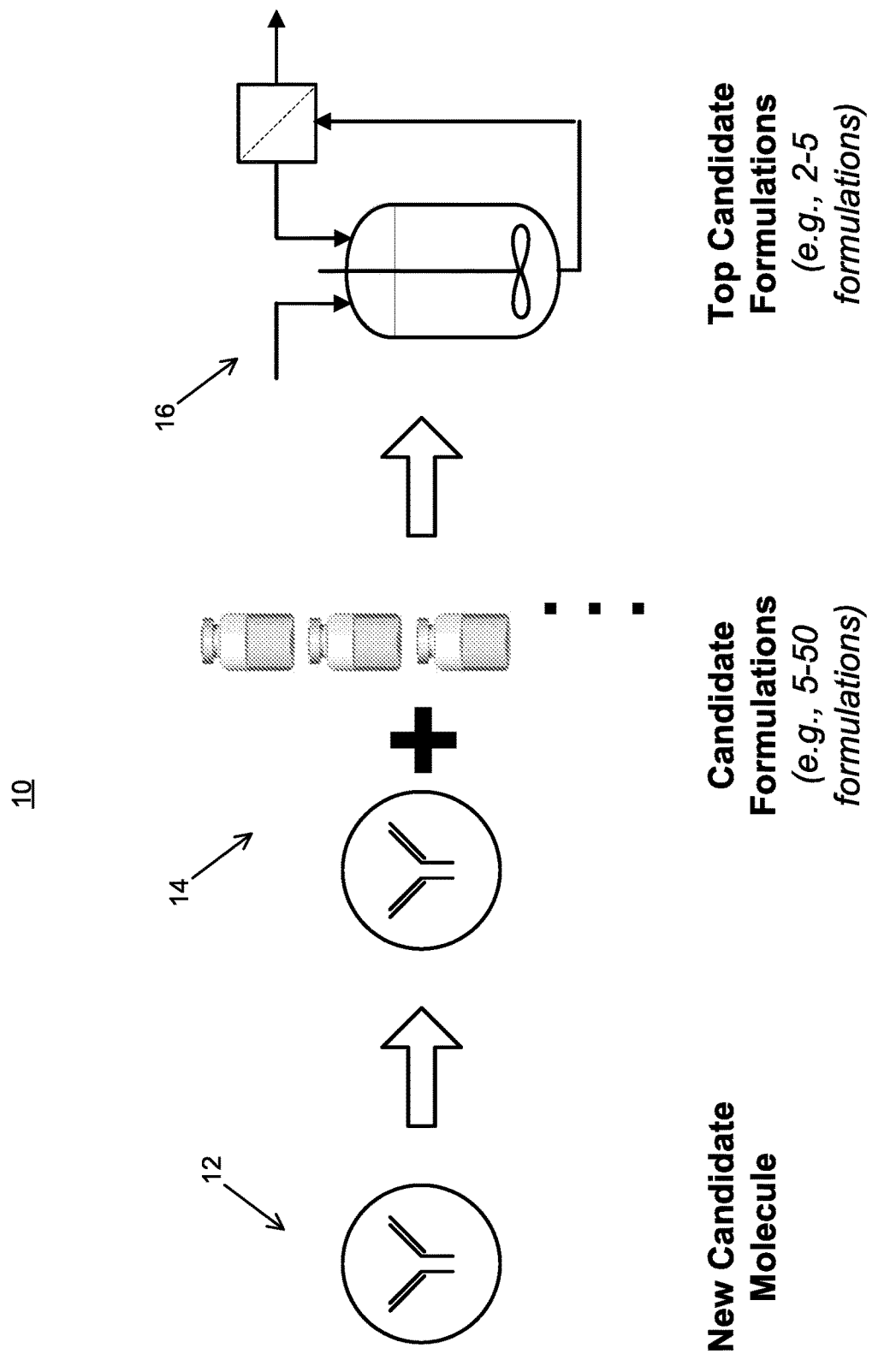
FIG. 1 depicts various stages of a typical formulation development process.

Operation of system 100, according to one embodiment, will now be described with reference to a specific scenario in which PFP prediction application 120 predicts the value of a protein formulation property for a particular set of inputs (formulation descriptors). This may be performed as a part of a formulation screening and optimization process (e.g., to provide a faster and more focused alternative to stage 14 and stage 16 of process 10 in FIG. 1), for example, or for research, development, validation, and/or other purposes.

Initially, computing system 102 trains (and validates) machine learning models 126, 128 using historical data stored in training database 130. Machine learning models 126, 128, including the features and labels on which their training may be based, are discussed in more detail below. Generally, however, models 126, 128 may collectively include one or more types of models. In one embodiment, at least prediction models 128 (and possibly also classification model 126) are regression models. For example, prediction models 128 and/or classification model 126 may be random forest models. Alternatively, or in addition, models 126, 128 may include support vector regression models, linear regression models, and/or other machine learning model types (e.g., neural networks). In some embodiments, interpretable models are used for model 126 and/or one or more (e.g., all) of models 128, in order to identify which inputs/features are most predictive of the model output. This may facilitate refinement of the inputs (i.e., the formulation descriptor set) for future use. For example, tree-based learning methods may output metrics indicative of how important each feature/descriptor is for purposes of reducing the mean square error of the model, when that feature/descriptor is used as a node in the decision tree. Moreover, coefficient plots can represent the normalized, directional coefficients that weight each feature/descriptor when predicting an output value or value range.

At a later time, when a user of client device 104 wishes to observe likely outcomes for one or more formulations (e.g., specific product molecule/excipient/solution combinations), he or she may utilize web browser application 146 to access a website hosted by computing system 102 via network 106. Computing system 102 may then cause web browser application 146 to present, via display 150, a GUI to the user. By operating user input device 152, the user may enter a set of formulation descriptors (e.g., product molecule identifier or properties, pH level, concentration, excipient type or properties, etc.) via the GUI, or may upload a file that includes the set of formulation descriptors. Data collection unit 122 receives the entered or uploaded set of descriptors, and provides the descriptors to prediction unit 124. Prediction unit 124 processes the set of descriptors using classification model 126 and one of prediction models 128 (e.g., as discussed below with reference to FIG. 3), and outputs a predicted protein formulation property (e.g., viscosity, or a stability metric such as a predicted size exclusion chromatography (SEC) peak percentage, etc.) at, and possibly also within a range of, the user-specified condition (e.g., at a user-specified concentration, and also at concentrations within a +/−10% range of the user-specified concentration, etc.). Prediction unit 124 provides the output to visualization unit 132, which causes web browser application 146 to update the GUI by presenting a visualization of the value, and/or other information derived from and/or related to the value, to the user via display 150. Example visualizations are discussed below with reference to FIGS. 6A and 6B.

The above process may be repeated for different sets of formulation descriptors, for the same molecule and/or for one or more other candidate molecules. For example, the user of client device 104 may enter or upload additional sets of formulation descriptors. For each descriptor set, data collection unit 122 may receive the descriptor set, and prediction unit 124 may predict a protein formulation property value. Visualization unit 132 may cause the GUI at client device 104 to present the results to the user on a case-by-case (i.e., descriptor set by descriptor set) basis, and/or may cause the GUI to present information that synthesizes the results of a number of different descriptor sets/predictions, as discussed further below.

Figure 3:
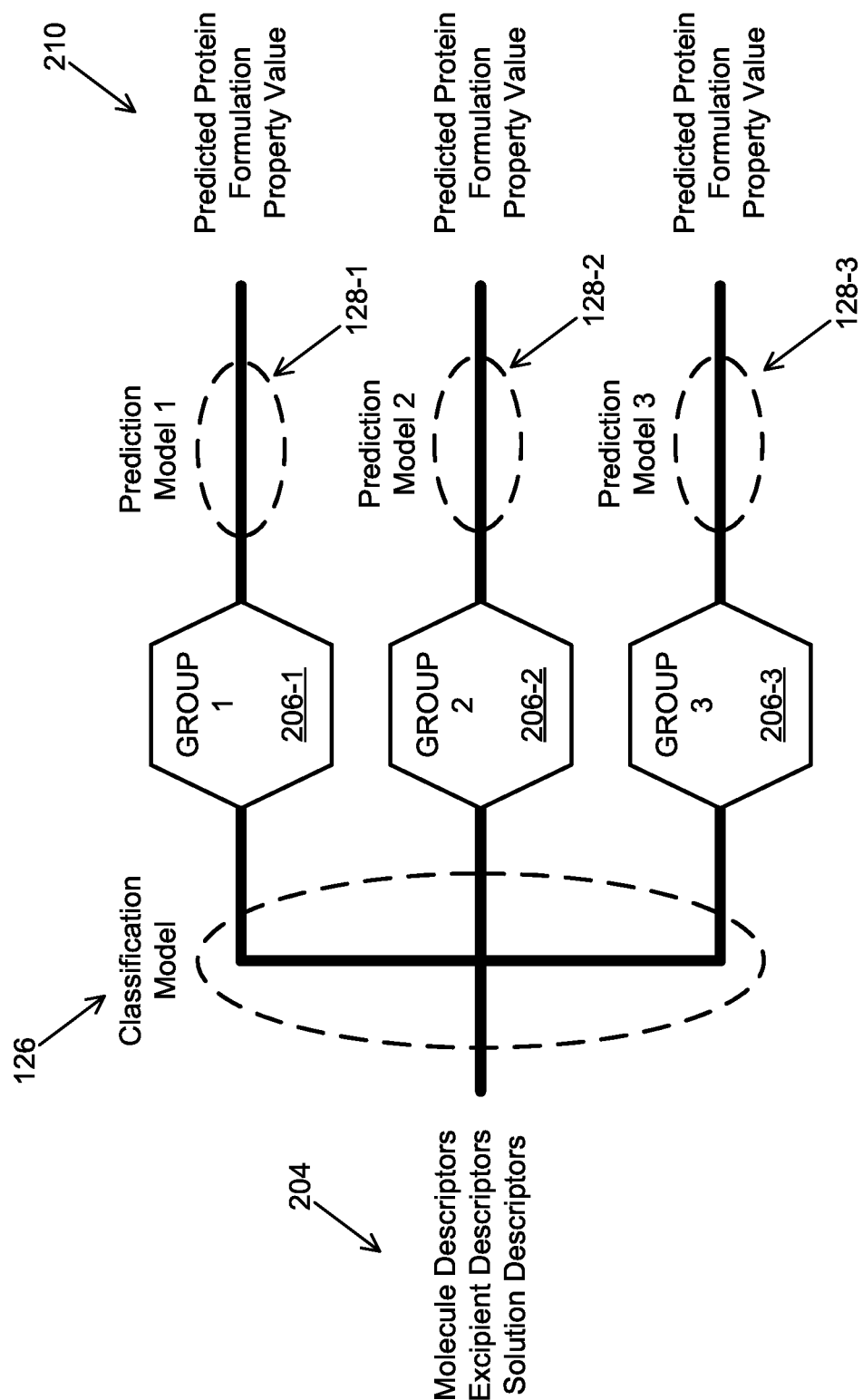
FIG. 3 depicts an example prediction architecture that may be implemented by the system of FIG. 2.

FIG. 3 depicts an example prediction architecture 200 that may be implemented by system 100, and more specifically by prediction unit 124. In architecture 200, a formulation descriptor set 204 represents a single set of formulation descriptors (i.e., descriptors for a single formulation) that was collected/received by data collection unit 122, and includes one or more molecule descriptors, one or more excipient descriptors, and/or one or more solution descriptors. Prediction unit 124 applies formulation descriptor set 204 as inputs to classification model 126, which classifies formulation descriptor set 204 as one of three pre-determined "groups" 206-1 through 206-3. Each of groups 206-1 through 206-3 corresponds to a different range of values for the protein formulation property being predicted, such as viscosity or a stability metric (e.g., a range of expected chromatography measurement values). For example, group 206-1 may correspond to viscosity values between 0 and 15 cP, group 206-2 may correspond to viscosity values between 15 and 45 cP, and group 206-3 may correspond to viscosity values greater than 45 cP (or between 45 and 100 cP, etc.). The three value ranges may or may not overlap, depending on the embodiment. In other embodiments, classification model 126 classifies the formulation descriptor set 204 into one of a different number of groups 206, such as two, four, five, ten, or any other suitable number of groups that is greater than one.

Thus, classification model 126 predicts a relatively broad range of protein formulation property values for the formulation descriptor set 204 that is under consideration. Prediction unit 124 then selects one of prediction models 128 (in this embodiment, one of prediction models 128-1 through 128-3) based on the classification (i.e., based on the group to which descriptor set 204 was assigned by classification model 126). Each of prediction models 128-1 through 128-3 is a model specifically trained to predict a protein formulation property value 210 for the range of values associated with the corresponding group 206. Thus, for example, if group 206-1 corresponds to a viscosity value range of 5-20 cP, prediction model 128-1 is a model specifically trained to predict viscosity values between (at least approximately) 5 and 20 cP. Similarly, if group 206-2 corresponds to a viscosity value range of 20-50 cP, prediction model 128-2 is a model specifically trained to predict viscosity values between (at least approximately) 20 and 50 cP, and so on. The "value" predicted by one of the models 128-1 through 128-3 may be a specific value (e.g., 6.7 cP). However, it is understood that in some embodiments, the "value" may be a relatively narrow range of values (e.g., 6-7 cP, or 6.5 cP +/−3%, etc.), so long as that range is substantially narrower than the value ranges corresponding to groups 206-1 through 206-3.

In some embodiments, classification model 126 and each of prediction models 128-1 through 128-3 all operate on the same inputs (i.e., the entire formulation descriptor set 204). In other embodiments, however, classification model 126 operates on a different (but possibly overlapping) subset of descriptor set 204 than do prediction models 128-1 through 128-3, and/or some or all of prediction models 128-1 through 128-3 operate on different (but possibly overlapping) subsets of descriptor set 204 as compared to each other.

The aforementioned functions of models 126, 128 determine the manner in which each model is trained. For example, classification model 126 may be trained using numerous training data sets that each include (1) a formulation descriptor set similar to descriptor set 204 (or a subset thereof that classification model 126 operates upon), and (2) a label indicating which value range (of the three ranges corresponding to groups 206-1 through 206-3) the formulation descriptor set fell into, as determined based on actual historical measurements. Conversely, each of prediction models 128-1 through 128-3 may be trained using training data sets that are specific to the value range of the corresponding group. For example, if group 206-1 corresponds to a viscosity value range of 0-20 cP, prediction model 128-1 may be trained using numerous training data sets that each include (1) a formulation descriptor set similar to descriptor set 204 (or a subset thereof that prediction model 128-1 operates upon), and (2) a label indicating the actual/historical measured value, falling within the range of 0 to 20 cP, for that formulation descriptor set.

As noted above, formulation descriptor set 204 may include one or more product molecule descriptors, one or more excipient descriptors, and/or one or more solution descriptors. Moreover, the descriptors may include categorical and/or numerical descriptors. However, determining which descriptors to include in set 204 (i.e., which descriptors will help achieve high accuracy predictions) is a non-trivial task. For example, a categorical molecule descriptor (e.g., "molecule X") may be appropriate if the molecule is well known and there is plenty of historical data to use for training (e.g., plenty of training data sets in which "molecule X" can be used as one input/feature). For new molecules, however, such training data may not exist, or may not exist in sufficient quantity to train a model well. In such cases, the patterns in the amino acid sequence, relative composition of amino acids and homology modeling (based on the amino acid sequence of the product molecule) may be used to determine more detailed categorical descriptors for the new molecule (e.g., particular types of chemical and/or structural properties, etc.), and/or to determine numerical descriptors for the new molecule (e.g., hydrophobic surface area or charge on specific regions, etc.). In some embodiments, many product molecule descriptors (e.g., hundreds of descriptors) may be used. An example process for deriving numerical product molecule descriptors is discussed below with reference to FIG. 4.

For the excipient, formulation descriptor set 204 may likewise use categorical and/or numerical descriptors. For example, descriptor set 204 may include a category/type of the excipient, such as "NaCl," "Creatinine," "Arginine," "Sarcosine," and so on. Other example excipient descriptors may include molecular weight (MW), charge, solubility, bonds, general category (e.g., surfactant vs. amino acid, etc.), and/or other suitable descriptors. An example process for deriving numerical excipient descriptors is discussed below with reference to FIG. 5. Formulation descriptor set 204 may also use categorical and/or numerical descriptors for the solution. For example, descriptor set 204 may include a pH level, a target concentration of the protein molecule in the solution, a buffer type, and so on.

In some embodiments, prediction unit 124 implements a separate version of architecture 200 for each of a number of different protein formulation properties. For example, prediction unit 124 may utilize a first set of classification and prediction models (arranged according to architecture 200) to predict a viscosity for formulation descriptor set 204, and also utilize a second set of classification and prediction models (also arranged according to architecture 200) to predict temporal/thermal changes in SEC and CEX (cation exchange chromatography) main peak percentage for formulation descriptor set 204.

Figure 4:
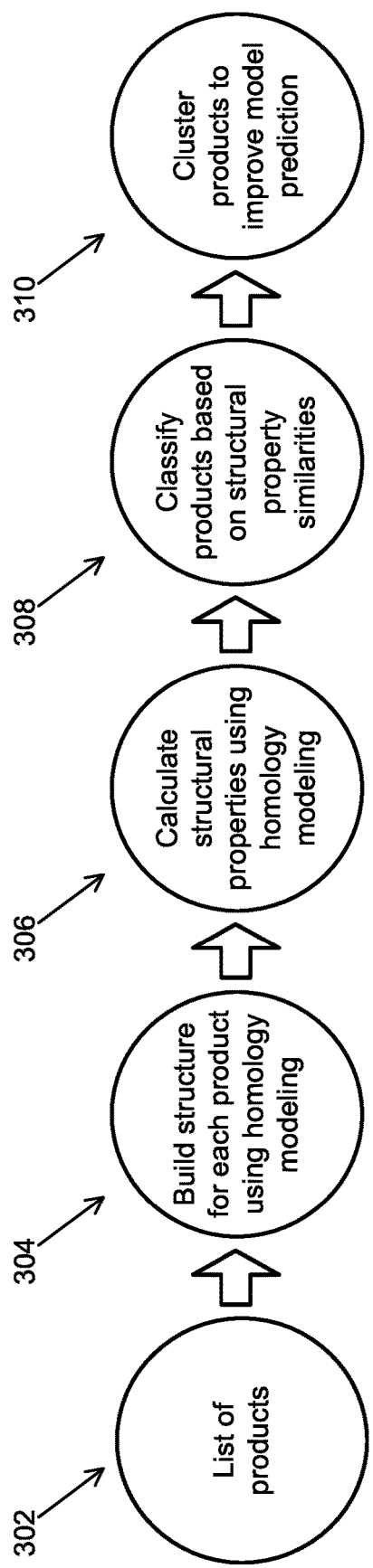
FIG. 4 depicts an example process for deriving numerical product molecule descriptors.

FIG. 4 depicts an example process 300 for deriving numerical product molecule descriptors. Determining these features is particularly challenging because proteins are very complex, high-dimensional systems, and sequence alignment in itself does not necessarily explain physical and chemical similarities between molecules. Moreover, first-principle studies have not fully discovered the relationships between viscosity and physical/chemical structure of the protein molecule, and the interaction between proteins and different excipients and solutions can result in unpredictable behavior.

In the example process 300, a list of products (protein molecules) of interest is assembled at an initial stage 302. The products may be known molecules for which a large amount of historical data exists, for example. Next, at stage 304, a structure is built for each product/molecule using homology modeling (e.g., molecular operating environment, or MOE, software). Stage 304 may include, for each molecule, a user entering the amino acid sequence of the molecule into the homology modeling software, and selecting an appropriate molecule template. The homology modeling software may then attempt to "fit" the amino acid sequence to the selected template.

At stage 306, for each product/molecule, the homology modeling software is used to calculate specific structural properties of the molecule. For example, the software may calculate molecule properties such as the van der Waals surface area of the molecule, the hydrophobic surface area of the molecule, and so on. In some embodiments, some or all of these properties are directly used as the product molecule descriptors in descriptor set 204. However, homology modeling software such as MOE can provide a large number of molecule properties (e.g., roughly 200 properties), which can greatly complicate the feature engineering process. Accordingly, additional stages of process 300 may be used to group different properties together using clustering and dimensionality reduction. In particular, at stage 308, the products/molecules are classified based on similarities of their structural properties and, at stage 310, the products/molecules are clustered using a suitable clustering algorithm (e.g., k-means clustering) and dimensionality reduction techniques (e.g., principal component analysis, or PCA). If the clustered groups tend to exhibit similar values for the protein formulation property being predicted (e.g., similar viscosity values), then the parameters that result from the dimensionality reduction (e.g., the weighted linear combinations of the molecule descriptors that were output by the homology modeling software) may be used as a part of descriptor set 204 for a particular molecule. In other embodiments, additional molecule information (e.g., apart from what is provided by MOE) and/or other information may also be considered in process 300, in order to improve the predictive power of the parameters that result from the clustering and dimensionality reduction. In some embodiments, process 300 is used merely to confirm whether currently used molecule descriptors are appropriate (i.e., have significant predictive power).

Figure 5:
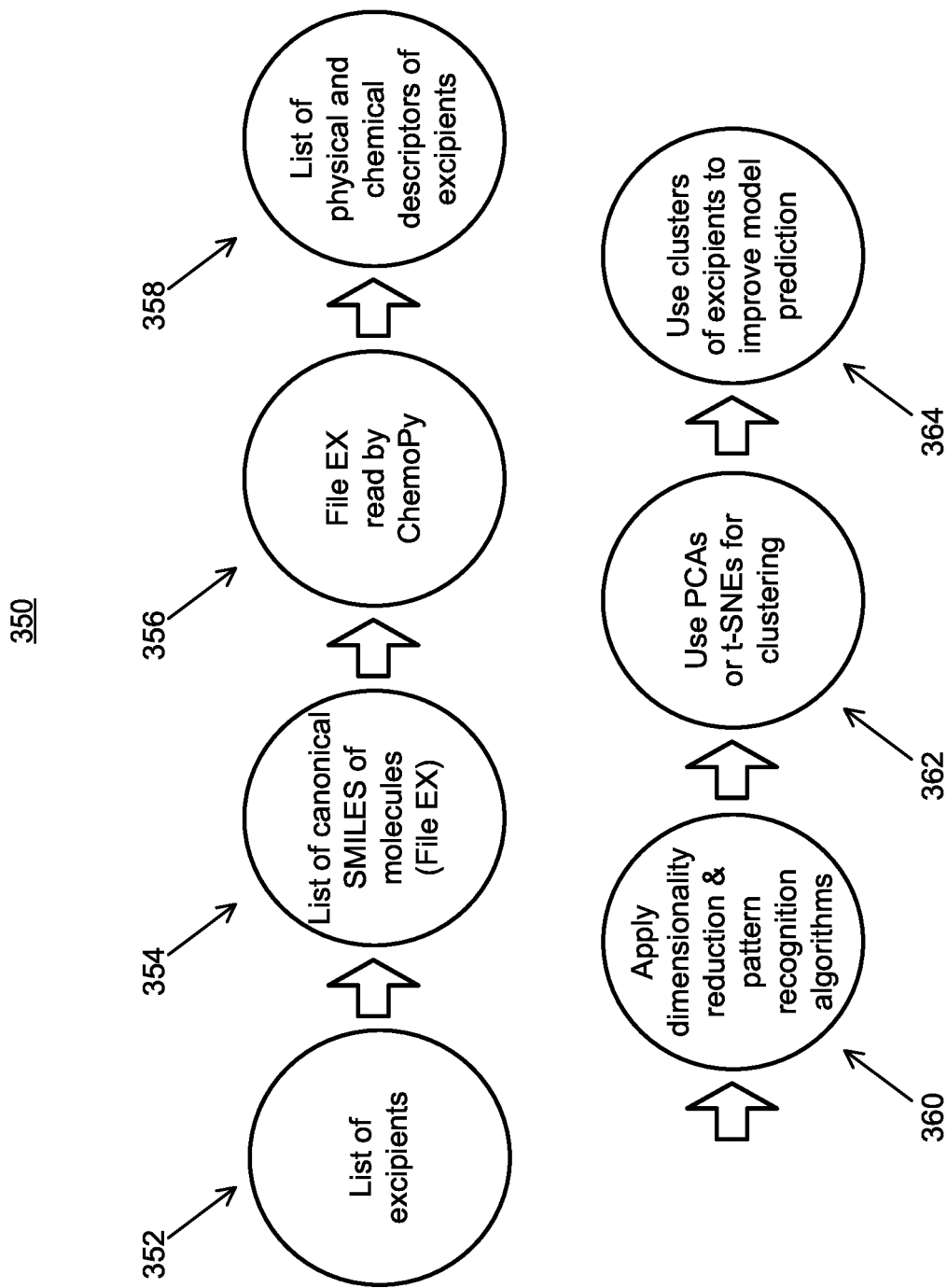
FIG. 5 depicts an example process for deriving numerical excipient descriptors.

FIG. 5 depicts an example process 350 for deriving numerical excipient descriptors. Initially, a list of excipients of interest is assembled at an initial stage 352. The excipients may be known excipients for which a large amount of historical data exists, for example. Next, at stage 354, a list of canonical SMILES of various molecules is assembled. "SMILES" stands for "simplified molecular-input line-entry system," and refers to a line notation for encoding molecular structures. The list of these line notations is assembled as a file denoted "file EX" in FIG. 5.

At stage 356, file EX is read by ChemoPy (an open source Python package), which produces at stage 358 a list of physical and chemical descriptors of the excipients that were listed at stage 352. At stage 360, dimensionality reduction and pattern recognition algorithms are applied to those physical and chemical descriptors, and techniques such as PCA or t-SNE (T-distributed stochastic neighbor embedding) are used to cluster the excipients at stage 362. Finally, at stage 364, the clusters of excipients are used to improve model prediction, e.g., by providing more, or narrowing in on, useful features/inputs to the machine learning models 126, 128. In some embodiments, process 350 is used merely to confirm whether currently used excipient descriptors are appropriate (i.e., have significant predictive power).

Figure 6A:
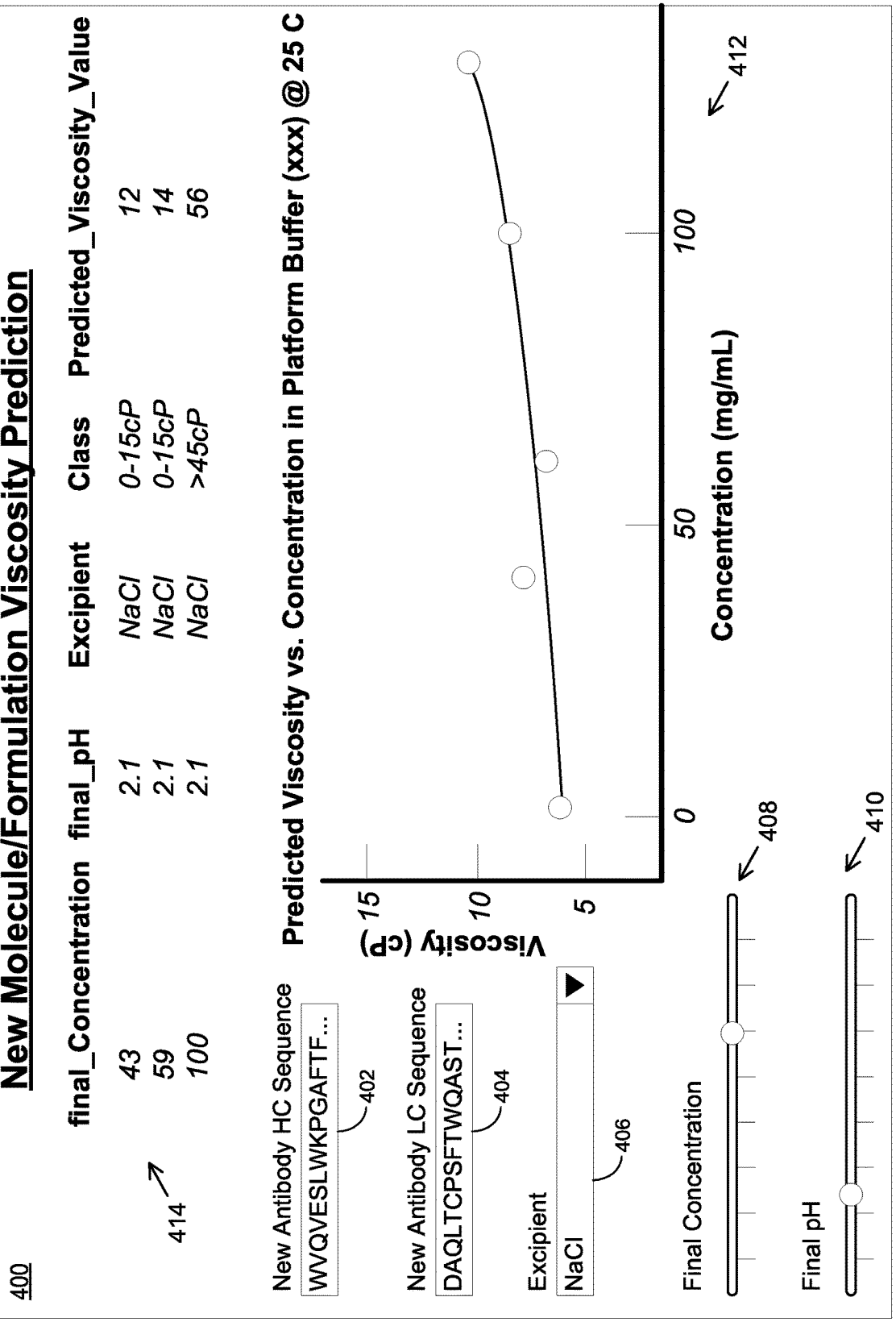
FIGS. 6A and 6B depict example graphical user interfaces that may be presented to a user of the client device of FIG. 2.
Figure 6B:
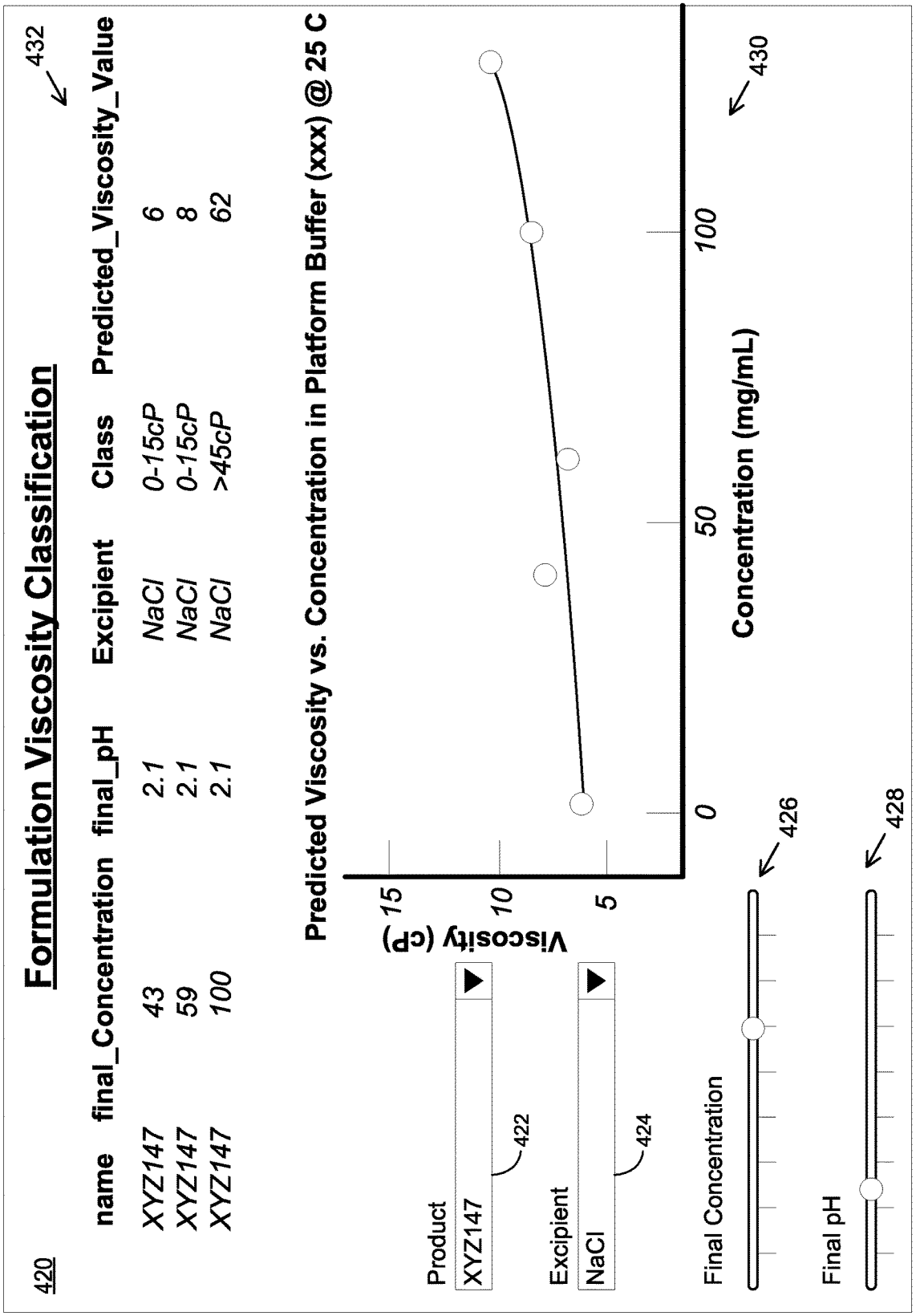

As noted above, visualization unit 132 generates one or more GUIs that enable users to enter or upload information (e.g., formulation descriptors) and/or to view displays indicative of the predictions provided by prediction unit 124 (and/or other information derived from those predictions). Some examples of these GUIs will now be described with reference to FIGS. 6A and 6B. While referred to below as separate GUIs, FIGS. 6A and 6B depict what may be separate GUIs or portions of the same GUI. The GUIs, or GUI portions, depicted in FIGS. 6A and 6B (and any other GUIs discussed below) may be generated by visualization unit 132, and/or may include content generated by visualization unit 132, and may be presented to the user of client device 104 via web browser application 146 and display 150 (e.g., after the data needed to populate, construct, and/or render the GUI is sent from computing system 102 to client device 104 via network 106 and network interfaces 112, 142).

Referring first to FIG. 6A, a GUI 400 provides a first interactive control/field 402 that enables the user to enter a heavy chain (HC) antibody sequence, a second interactive control/field 404 that enables the user to enter a light chain (LC) antibody sequence, a third interactive control/field 406 that enables the user to enter an excipient type, a fourth interactive control (e.g., a slide control or radio buttons) 408 that enables the user to enter a target protein concentration, and a fifth interactive control (e.g., a slide control or radio buttons) 410 that enables the user to enter a target pH level or range. The values and/or ranges that the user enters via controls 402, 404, 406, 408 and 410 may be used as (and/or may be used to derive) the formulation descriptor set 204. Alternatively, or in addition, the GUI 400 may include one or more interactive controls that enable the user to upload a file that defines some or all of the formulation descriptor set 204. The GUI may also include an interactive control (e.g., button) that enables the user to obtain a prediction (e.g., viscosity value) for the entered descriptors. For example, activation of the control may cause prediction unit 124 to apply the entered descriptors as inputs to the various models 126, 128 of architecture 200, in the manner discussed above in connection with FIG. 3.

In the example embodiment of FIG. 6A, the GUI 400 also presents predictions/outputs in a graph 412 that plots protein concentration (e.g., in mg/mL) against predicted viscosity (e.g., in cP) for a given formulation, and a corresponding table 414 that lists those values, other descriptors (pH, excipient type), and predicted class (viscosity range). For example, the different concentrations plotted in graph 412, and the descriptors shown in table 414, may be values selected by the user via interactive controls 406, 408, 410.

The "class" of table 414 may be the output of classification model 126, and the predicted viscosity value of table 414 and graph 412 may be the output of the appropriate one of prediction models 128-1 through 128-3, for example.

FIG. 6B depicts a GUI 420 that provides a first interactive control/field 422 that enables the user to enter an identifier of the product/protein/molecule, a second interactive control/field 424 that enables the user to enter the excipient type, a third interactive control/field 426 (e.g., a slide control or radio buttons) 426 that enables the user to enter a target protein concentration, and a fourth interactive control (e.g., a slide control or radio buttons) 428 that enables the user to enter a target pH level or range. Similar to the GUI 400 of FIG. 6A, the GUI 420 includes a graph 430 and a table 432 to present predicted viscosity values, descriptor values, and (in table 432) the predicted class (viscosity range). In some use cases, the molecule for which predictions are being made is one not yet known to the system, and therefore the interactive control 422 may not include an associated identifier. Thus, in some embodiments, the GUI 432 includes one or more other controls that enable a user to enter other information descriptive of the molecule (e.g., various numerical and/or categorical descriptors, as discussed above).

Other visualizations are also possible. For example, a GUI may present a histogram plotting frequency versus protein concentration (or frequency versus viscosity, etc.), with "frequency" referring to the number of different formulations at a given concentration (or viscosity, etc.) value with which the model was trained. The results may all correspond to the same excipient and solution descriptors, or may encompass multiple combinations of excipient and solution descriptors, for example. As another example, a visualization (e.g., in a separate GUI) may display a rank-ordering of excipient/solution formulations for a specific molecule (e.g., ranked according to predicted viscosity, with lower viscosity values corresponding to a higher rank). Moreover, the visualizations may instead, or additionally, present predictions of other formulation properties (e.g., SEC and/or CEX readings, etc.). Generally, system 100 may include any suitable tools that enable the user of client device 104 to identify the top/best formulations for a given product molecule, or across multiple product molecules, based on a given set of criteria. The tools may be highly customizable, such that users can view any combination of data that may be helpful for purposes of identifying the best formulations, and/or for validation or research purposes.

Figure 7:
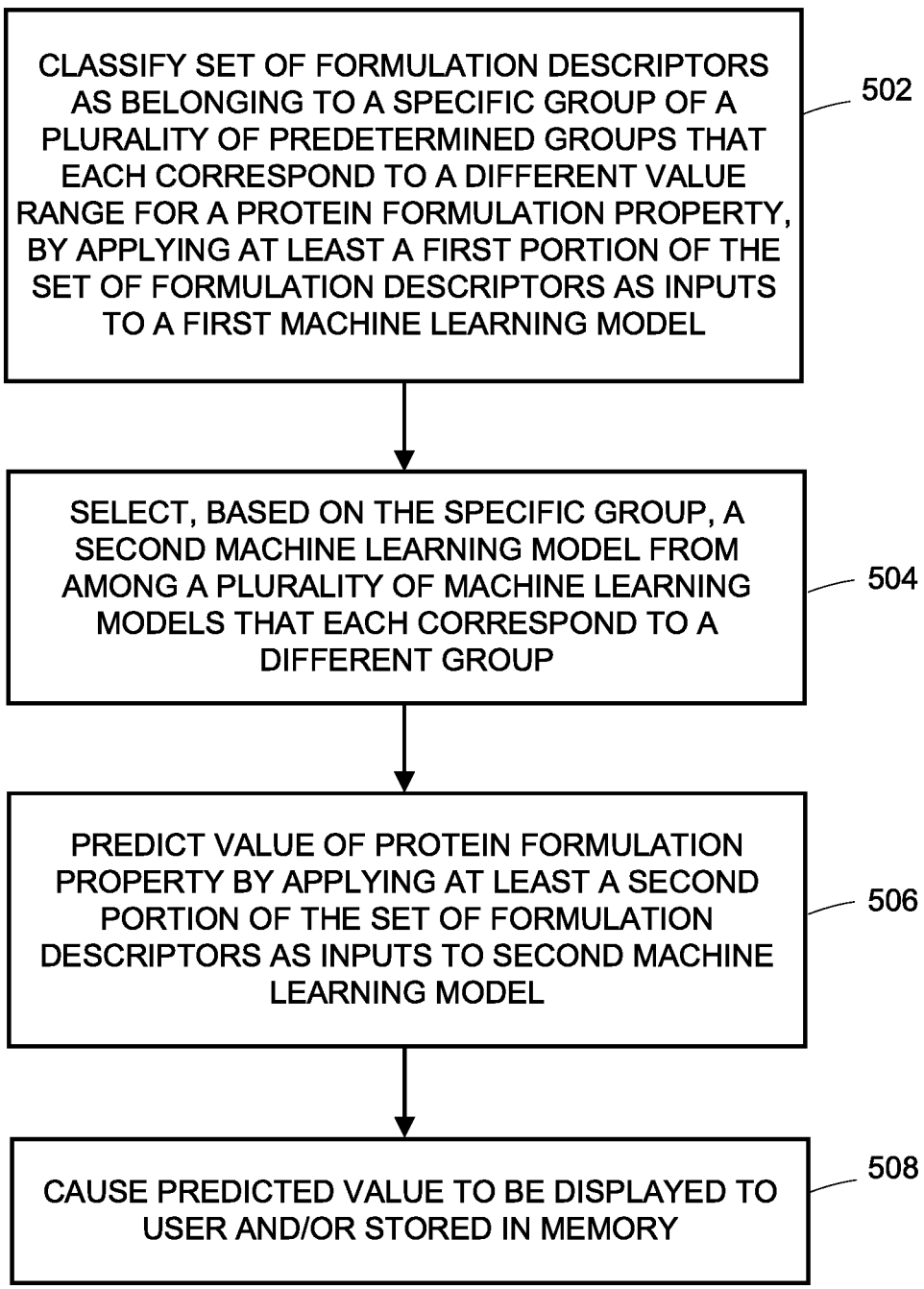
FIG. 7 is a flow diagram of an example method for predicting a property of potential protein formulations.

FIG. 7 is a flow diagram of an example method 500 for screening candidate protein formulations. The method 500 may be implemented by processing unit 110 of computing system 102 when executing the software instructions of PFP protein application 120 stored in memory unit 114, for example.

At block 502, a set of formulation descriptors (e.g., descriptor set 204) is classified as belonging to a specific group of a plurality of predetermined groups (e.g., groups 206-1 through 206-3, or more generally any suitable number of groups greater than one), with each of the predetermined groups corresponding to a different value range for a protein formulation property. The formulation descriptors may include one or more molecule descriptors (e.g., molecule identifier, monoclonal versus bi-specific antibody type, outputs from a homology modeling tool such as MOE, etc.), one or more excipient descriptors (e.g., excipient identifier, etc.), and/or one or more solution descriptors (e.g., target pH level, target protein concentration, etc.), for example, and may include categorical and/or numerical values. The protein formulation property may be viscosity, for example, or a stability metric such as a size-exclusion chromatography (SEC) reading (e.g., SEC main peak percentage, SEC low molecular weight peak percentage, or SEC high molecular weight peak percentage, including absolute readings and the rate of change as a function of time or temperature) or a CEX reading, etc.

Block 502 includes applying at least a first portion (and possibly all) of the set of formulation descriptors as inputs to a first machine learning model (e.g., classification model 126). The first machine learning model may be a classification or a regression model (e.g., a random forest or support vector regression model), or any other suitable type of machine learning model.

At block 504, a second machine learning model is selected from among a plurality of machine learning models (e.g., prediction models 128-1 through 128-3) that each correspond to a different one of the predetermined groups, with the selection at block 504 being based on the specific group resulting from the classification at block 502. The second machine learning model, and each of the plurality of machine learning models generally, may be a regression model (e.g., a random forest or support vector regression model), or any other suitable type of machine learning model.

At block 506, a value of the protein formulation property (e.g., viscosity) is predicted by applying at least a second portion (and possibly all) of the set of formulation descriptors as inputs to the second machine learning model that was selected at block 504. The first and second portions of the set of formulation descriptors may be partially overlapping or non-overlapping subsets of the set of formulation descriptors, or may each be the entirety of the set of formulation descriptors.

At block 508, the value predicted at block 506 is caused to be displayed to a user and/or stored in a memory. Block 508 may include generating data needed to create and/or populate a GUI (e.g., data for populating various graphs, tables and/or fields of the GUI, and possibly also data defining the presentation/format of the GUI), and sending that data to a client device (e.g., to client device 104 via network 106) for display at the client device (e.g., on display 150). As other examples, block 508 may instead, or also, include causing a local display to present the value, and/or storing the value in a local memory (e.g., memory unit 114). As yet another example, block 508 may include sending the value to another computing device (e.g., to client device 104 via network 106) to cause the other computing device to store the value in a memory (e.g., in memory unit 144).

In some embodiments, method 500 includes one or more additional blocks not shown in FIG. 7. For example, method 500 may include an additional block, occurring prior to block 502, at which the set of formulation descriptors is received from a user via a GUI (e.g., after the user enters the descriptors using interactive controls such as those discussed above in connection with FIGS. 6A and 6B). As another example, method 500 may include a first additional block, occurring at some point after block 506, at which a rank-ordering of a plurality of candidate protein formulations is determined based in part on the value predicted at block 506, and a second additional block at which an indication of the rank-ordering is caused to be displayed to the user via a GUI.

Although the systems, methods, devices, and components thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A method of predicting a property of potential protein formulations, the method comprising:
classifying, by one or more processors of a computing system, a set of formulation descriptors as belonging to a specific group of a plurality of predetermined groups that each correspond to a different value range for a protein formulation property, wherein classifying the set of formulation descriptors includes applying at least a first portion of the set of formulation descriptors as inputs to a first machine learning model;
selecting, by the one or more processors and based on the specific group, a second machine learning model from among a plurality of machine learning models that each correspond to a different one of the plurality of predetermined groups;
predicting, by the one or more processors, a value of the protein formulation property by applying at least a second portion of the set of formulation descriptors as inputs to the second machine learning model; and
causing, by the one or more processors, the value of the protein formulation property to be one or both of (i) displayed to a user, and (ii) stored in a memory.

2. The method of claim 1, wherein the protein formulation property is viscosity, and wherein each group of the plurality of predetermined groups corresponds to a different range of viscosity values.

3. The method of claim 1, wherein the set of formulation descriptors includes (i) one or more molecule descriptors, (ii) one or more excipient descriptors, and (iii) one or more solution descriptors.

4. The method of claim 1, wherein the set of formulation descriptors includes one or more numerical values.

5. The method of claim 1, wherein the set of formulation descriptors includes one or more categories.

6. The method of claim 1, wherein the set of formulation descriptors includes one or more of (i) a molecule identifier, (ii) an antibody type, (iii) a target pH level, and (iv) a target protein concentration.

7. The method of claim 1, wherein the set of formulation descriptors includes one or more of (i) molecular weight of an excipient, (ii) charge of the excipient, (iii) solubility of the excipient, (iv) bonds of the excipient, and (v) a type of the excipient.

8. The method of claim 1, wherein the plurality of predetermined groups consists of three groups.

9. The method of claim 1, wherein each of the plurality of machine learning models includes a regression and/or classification model.

10. The method of claim 9, wherein at least one of the plurality of machine learning models is a random forest model.

11. The method of claim 1, wherein:
classifying the set of formulation descriptors includes applying the set of formulation descriptors as inputs to the first machine learning model; and
predicting the value of the protein formulation property includes applying the set of formulation descriptors as inputs to the second machine learning model.

12. The method of claim 1, further comprising:
receiving, by the one or more processors and via a first graphical user interface, the set of formulation descriptors from a user.

13. The method of claim 12, further comprising:
determining, by the one or more processors and based in part on the predicted value of the protein formulation property, a rank-ordering of a plurality of candidate protein formulations; and
causing, by the one or more processors, an indication of the rank-ordering to be displayed via the first graphical user interface or a second graphical user interface.

14. A computing system comprising:
one or more processors; and
one or more memories storing instructions that, when executed by the one or more processors, cause the computing system to
classify a set of formulation descriptors as belonging to a specific group of a plurality of predetermined groups that each correspond to a different value range for a protein formulation property, wherein classifying the set of formulation descriptors includes applying at least a first portion of the set of formulation descriptors as inputs to a first machine learning model,
select, based on the specific group, a second machine learning model from among a plurality of machine learning models that each correspond to a different one of the plurality of predetermined groups,
predict a value of the protein formulation property by applying at least a second portion of the set of formulation descriptors as inputs to the second machine learning model, and
cause the value of the protein formulation property to be one or both of (i) displayed to a user, and (ii) stored in a memory.

15. The computing system of claim 14, wherein the protein formulation property is viscosity, and wherein each group of the plurality of predetermined groups corresponds to a different range of viscosity values.

16. The computing system of claim 14, wherein the set of formulation descriptors includes (i) one or more molecule descriptors, (ii) one or more excipient descriptors, and (iii) one or more solution descriptors.

17. The computing system of claim 14, wherein each of the plurality of machine learning models is a regression and/or classification model.

18. The computing system of claim 17, wherein at least one of the plurality of machine learning models is a random forest model.

19. A non-transitory computer-readable medium storing instructions that, when executed by one or more processors of a computing system, cause the computing system to:
classify a set of formulation descriptors as belonging to a specific group of a plurality of predetermined groups that each correspond to a different value range for a protein formulation property, wherein classifying the set of formulation descriptors includes applying at least a first portion of the set of formulation descriptors as inputs to a first machine learning model;

select, based on the specific group, a second machine learning model from among a plurality of machine learning models that each correspond to a different one of the plurality of predetermined groups;
predict a value of the protein formulation property by applying at least a second portion of the set of formulation descriptors as inputs to the second machine learning model; and
cause the value of the protein formulation property to be one or both of (i) displayed to a user, and (ii) stored in a memory.

20. The non-transitory computer-readable medium of claim 19, wherein:
the protein formulation property is viscosity;
each group of the plurality of predetermined groups corresponds to a different range of viscosity values; and
the set of formulation descriptors includes (i) one or more molecule descriptors, (ii) one or more excipient descriptors, and (iii) one or more solution descriptors.

21. The non-transitory computer-readable medium of claim 19, wherein:
each of the plurality of machine learning models is a regression and/or classification model; and
at least one of the plurality of machine learning models is a random forest model.

* * * * *